US010537893B2

(12) United States Patent
Yamano

(10) Patent No.: US 10,537,893 B2
(45) Date of Patent: Jan. 21, 2020

(54) AUTOMATIC ANALYSIS APPARATUS

(71) Applicant: HITACHI HIGH-TECHNOLOGIES CORPORATION, Tokyo (JP)

(72) Inventor: Teruhiro Yamano, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 372 days.

(21) Appl. No.: 15/320,019

(22) PCT Filed: May 12, 2015

(86) PCT No.: PCT/JP2015/063685
§ 371 (c)(1),
(2) Date: Dec. 19, 2016

(87) PCT Pub. No.: WO2015/198730
PCT Pub. Date: Dec. 30, 2015

(65) Prior Publication Data
US 2017/0151570 A1    Jun. 1, 2017

(30) Foreign Application Priority Data
Jun. 26, 2014 (JP) .................. 2014-131775

(51) Int. Cl.
B01L 3/00         (2006.01)
G01N 21/51        (2006.01)
(Continued)

(52) U.S. Cl.
CPC ............ B01L 3/52 (2013.01); G01N 21/51 (2013.01); G01N 21/59 (2013.01);
(Continued)

(58) Field of Classification Search
CPC ....... G01N 2035/1025; G01N 35/1002; G01N 35/0099
(Continued)

(56) References Cited

U.S. PATENT DOCUMENTS 4,451,433 A * 5/1984 Yamashita ....... G01N 35/00663
422/509
2009/0220383 A1   9/2009 Iijima et al.
2012/0114526 A1 * 5/2012 Watanabe ............... G01F 23/00
422/63

FOREIGN PATENT DOCUMENTS

EP    0 235 778 A2    9/1987
JP    04-232865 A     8/1992
(Continued)

OTHER PUBLICATIONS

International Search Report of PCT/JP2015/063685 dated Jul. 28, 2015.
(Continued)

Primary Examiner — Natalia Levkovich
(74) Attorney, Agent, or Firm — Mattingly & Malur, PC

(57) ABSTRACT

An automatic analysis apparatus is capable of replacing circulated water in a reaction vessel and continuously cooling a light source lamp without stopping an operation for measuring a specimen. In an operation state, a drain electromagnetic valve 49 is opened to drain reaction vessel water outside and when the water level reaches a measurement limit water level, the drain electromagnetic valve 49 is closed. The reaction vessel water is supplied by starting a water supply pump, opening a water supply electromagnetic valve and when the water level has reached a full water level, the water supply electromagnetic valve is closed, and the water supply pump is stopped. In a state other than the operation state, the reaction vessel water is drained outside. When the water level has reached a circulation limit water level, the drain electromagnetic valve is closed.

9 Claims, 4 Drawing Sheets

(51) Int. Cl.
*G01N 21/59* (2006.01)
*G01N 35/00* (2006.01)

(52) U.S. Cl.
CPC .... *G01N 35/00712* (2013.01); *B01L 2200/16* (2013.01); *B01L 2300/0627* (2013.01); *G01N 2021/513* (2013.01)

(58) Field of Classification Search
USPC .................................................. 422/509, 517
See application file for complete search history.

(56) References Cited

FOREIGN PATENT DOCUMENTS

| | | |
|---|---|---|
| JP | 05-288657 A | 11/1993 |
| JP | 2003-294763 A | 10/2003 |
| JP | 2004-251802 A | 9/2004 |
| JP | 2007-248413 A | 9/2007 |
| JP | 4185859 B2 | 11/2008 |
| JP | 2010-139332 A | 6/2010 |
| JP | 2012-103183 | 5/2012 |
| JP | 2014-16208 A | 1/2014 |

OTHER PUBLICATIONS

Extended European Search Report received in corresponding European Application No. 15812479.2 dated Jan. 25, 2018.
Chinese Office Action received in corresponding Chinese Application No. 2015800335845 dated Oct. 23, 2017.
International Preliminary Report on Patentability received in corresponding International Application No. PCT/JP2015/063685 dated Jan. 5, 2017.

* cited by examiner

AUTOMATIC ANALYSIS APPARATUS

TECHNICAL FIELD

The present invention relates to an automatic analysis apparatus for irradiating an object to be measured with light and measuring the light scattered by the object to be measured at a plurality of wavelengths.

BACKGROUND ART

In the automatic analysis apparatus, circulated water stored in a reaction vessel and light which has passed through the object to be measured are measured. Therefore, when foreign substances such as forms and dusts are mixed into the circulated water in the reaction vessel, a noise is detected since the light is scattered by the foreign substances. Then, the noise affects the measurement results.

To remove the foreign substances, for example, it is necessary to replace water in the reaction vessel once in every 24 hours as a maintenance operation.

PTL 1 discloses a technique for removing foams in thermostatic bath water as a method for removing the foreign substances.

CITATION LIST

Patent Literature

PTL 1: JP 4185859 B2

SUMMARY OF INVENTION

Technical Problem

Normally, in order to reduce water consumption, in a procedure to replace water in the reaction vessel of the automatic analysis apparatus, the circulated water in the reaction vessel is concurrently drained, and after that, the water is supplied. At this time, in a case where the temperature of the reaction vessel is maintained to be constant, a time to heat the supplied water is required.

Also, in a case where a light source lamp for measurement is cooled with the circulated water, the cold storage of the light source lamp is stopped when the circulated water is concurrently drained. Since the light source lamp cannot be cooled, the light source lamp is temporarily turned off. In this case, to turn on the photometer again and to perform stable measurement, extra periods of time to heat the supplied water and to stabilize the light source lamp are needed as a maintenance time.

In recent years, an automatic analysis apparatus has been desired which can be continuously operated for a week, not for 24 hours. In an operation, the light source lamp is turned off to replace the water in the reaction vessel and the measurement of the specimen with the photometer is temporarily stopped. This operation wastes time. Also, the continuous operation is interrupted. Therefore, it has been desired to avoid this maintenance operation.

A purpose of the present invention is to realize an automatic analysis apparatus capable of replacing circulated water in a reaction vessel and continuously cooling a light source lamp without stopping an operation for measuring a specimen.

Solution to Problem

To achieve the above purpose, the present invention is configured as follows.

An automatic analysis apparatus includes a reaction container moving mechanism which has a plurality of reaction containers, for containing a specimen and a reagent, arranged therein, has a reaction vessel to immerse the reaction container in the water, and moves the reaction containers, a light source lamp which irradiates the reaction container arranged in the reaction vessel of the reaction container moving mechanism with light, a photometer which measures the light emitted from the light source lamp and passed through the reaction container, a discharge mechanism which discharges the water in the reaction vessel, a water supply mechanism which supplies the water in the reaction vessel, a reaction vessel water level detector which includes a first water level detector for detecting that the water level of the water in the reaction vessel is a full water level and a second water level detector for sensing that the water level of the water in the reaction vessel is a measurement limit water level which is lower than the full water level and higher than a position of an optical axis of the light emitted from the light source lamp, and a control unit which controls operations of the reaction container moving mechanism, the light source lamp, and the photometer and analyzes the specimen in the reaction container.

The control unit controls operations of the discharge mechanism and the water supply mechanism based on the water level of the reaction vessel water detected by the reaction vessel water level detector.

Advantageous Effects of Invention

An automatic analysis apparatus can be realized which can replace circulated water in a reaction vessel and can continuously cool a light source lamp without stopping an operation for measuring a specimen.

DESCRIPTION OF EMBODIMENTS

An embodiment of the present invention is described below with reference to the attached drawings.

Embodiment

Figure 1:
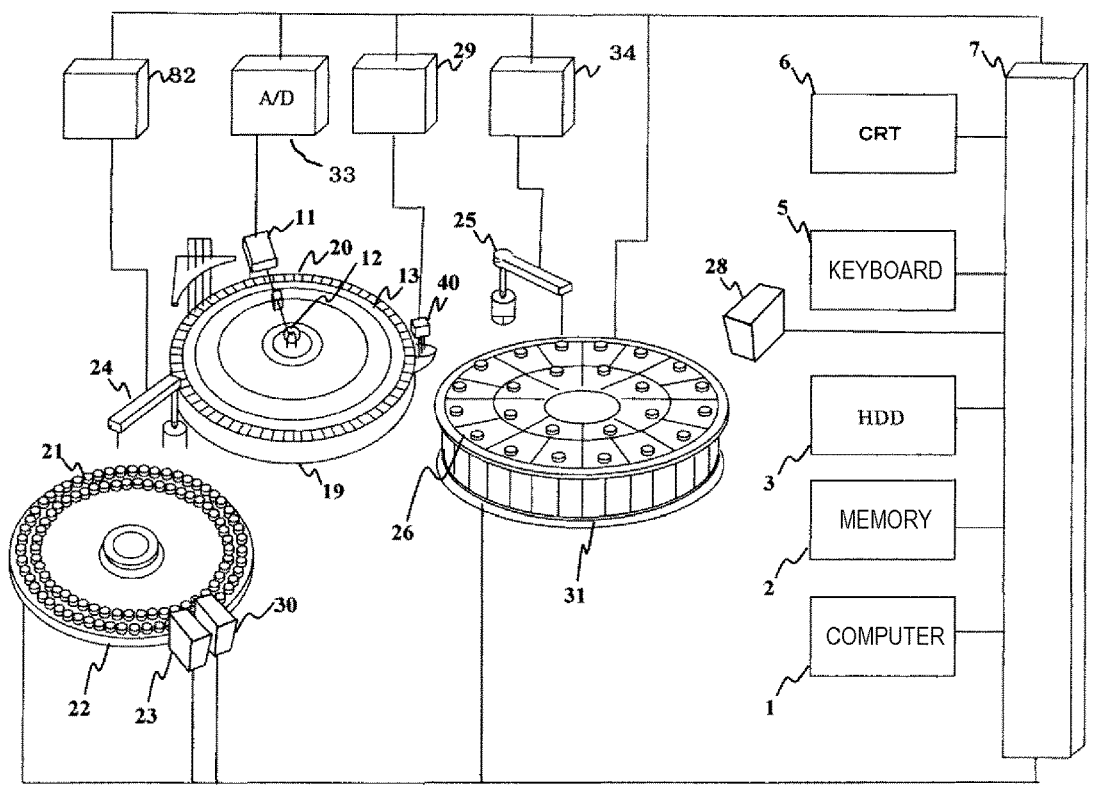
FIG. 1 is a schematic diagram of an entire structure of an automatic analysis apparatus to which one embodiment of the present invention is applied.

FIG. 1 is a schematic diagram of an entire structure of an automatic analysis apparatus to which one embodiment of the present invention is applied. The automatic analysis apparatus is a multi-item chemical analysis apparatus for analyzing a plurality of analysis items of a specimen sample with a photometric system.

Multiple specimen containers 21 for containing specimens are arranged in a specimen moving mechanism (specimen disk) 22 in FIG. 1. The specimen suctioned by a specimen dispenser 24 is discharged to a reaction container 20 arranged in a reaction container moving mechanism (reaction disk) 13.

Here, the reaction vessel 19 is filled with reaction vessel water, and a lower part of the reaction container 20 is immersed in the reaction vessel water in the reaction vessel 19. An electrostatic capacitance type reaction vessel water level detector 40 detects a water level of the reaction vessel water. The reaction vessel water level detector 40 is connected to a computer 1 via an A/D converter 29 and an interface 7. The reaction container moving mechanism 13 intermittently rotates at a constant cycle. The reaction container 20 crosses an optical axis 47 of light output from a light source lamp 12 (illustrated in FIG. 2) every time the reaction container moving mechanism 13 rotates. When the reaction container 20 crosses the optical axis 47, a photometer 11 measures an absorbance of a content in the reaction container 20.

In the reaction container 20, the absorbance of cell blank water is measured by previously dispensing water before the specimen is dispensed.

In parallel to this, a reagent container 26 for containing a reagent used for analyzing the specimen is moved to a position under a reagent dispenser 25 by a first reagent moving mechanism 31. After that, a color reaction is generated by suctioning the reagent from the reagent container 26 with the reagent dispenser 25 and discharging it to the reaction container 20. When the reaction container 20 in which the color reaction is generated crosses the optical axis 47 of the light output from the light source lamp 12 every time the reaction container moving mechanism 13 rotates, the photometer 11 measures the absorbance.

The absorbance measured by the photometer 11 is supplied to the computer 1 via an A/D converter 33 and the interface 7. The computer 1 calculates a component concentration of the specimen by using the supplied absorbance.

Also, after the reaction vessel water has been replaced, the absorbances of the cell blank water in all the reaction containers 20 are measured, and the absorbances are stored in a memory 2 as reference values. The absorbance of the cell blank water in each reaction container 20 is measured before the specimen is dispensed. By comparing the absorbance with the reference value, a state of a measurement system including the reaction container 20, the reaction vessel water, the light source lamp 12, and the photometer 11 is monitored.

A specimen information reader/writer 23 reads/writes information on the specimen in the specimen container 21 arranged in the specimen moving mechanism 22. A specimen container height detector 30 detects a height of the specimen container 21 arranged in the specimen moving mechanism 22. A reagent information reader/writer 28 reads/writes information on the reagent in the reagent container 26 arranged in the reagent moving mechanism 31.

The specimen information reader/writer 23, the specimen container height detector 30, and the reagent information reader/writer 28 are connected to the computer 1, the memory 2, a HDD 3, and a CRT (display unit) 6 via the interface 7.

Also, the specimen dispenser 24 is connected to a driving unit 32, and the driving unit 32 controls an operation of the specimen dispenser 24 by an instruction from the computer 1 supplied via the interface 7. Also, the reagent dispenser 25 is connected to a driving unit 34, and the driving unit 34 controls an operation of the reagent dispenser 25 by an instruction from the computer 1 supplied via the interface 7.

Also, a keyboard 5 is connected to the interface 7, and an operation instruction and the like are input to the computer 1 and the like.

Figure 2:
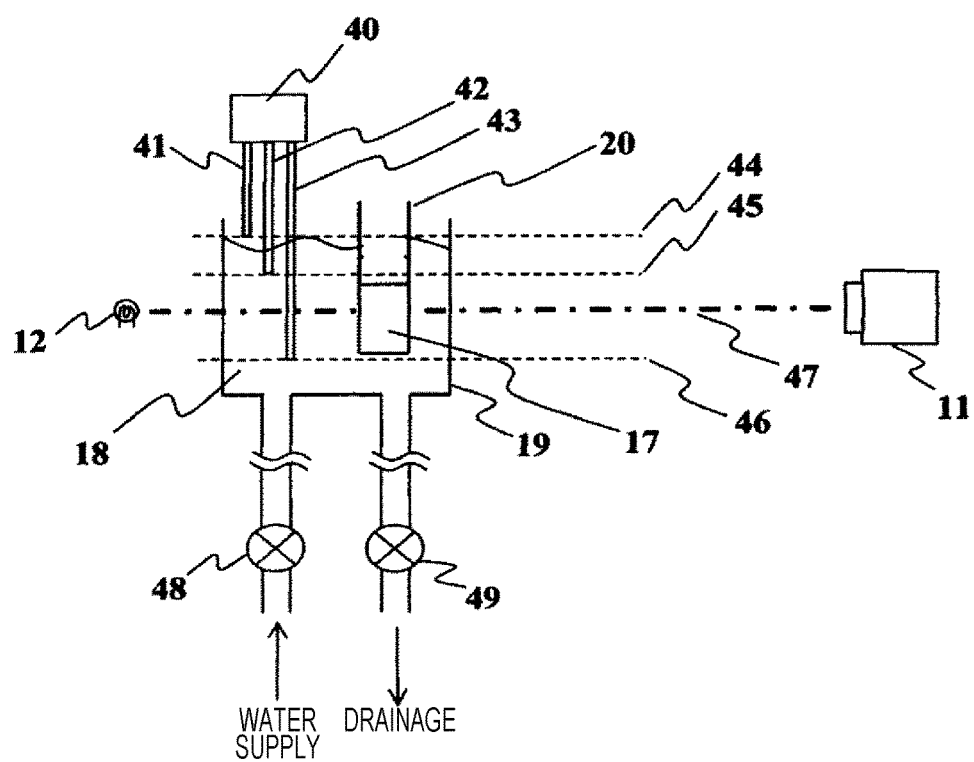
FIG. 2 is a diagram to describe replacement of reaction vessel water in a reaction vessel of the automatic analysis apparatus according to one embodiment of the present invention.

FIG. 2 is a diagram to describe replacement of reaction vessel water 18 in the reaction vessel 19 illustrated in FIG. 1. In FIG. 2, the reaction vessel water level detector 40 includes a first water level detector 41, a second water level detector 42, and a third water level detector 43 and can detect water levels of three stages.

The reaction vessel water 18 is circulated constant temperature water from a thermostatic bath of which a temperature is maintained to be constant (normally, 37° C.). The plurality of reaction containers 20 is immersed in this circulated constant temperature water.

Figure 3:
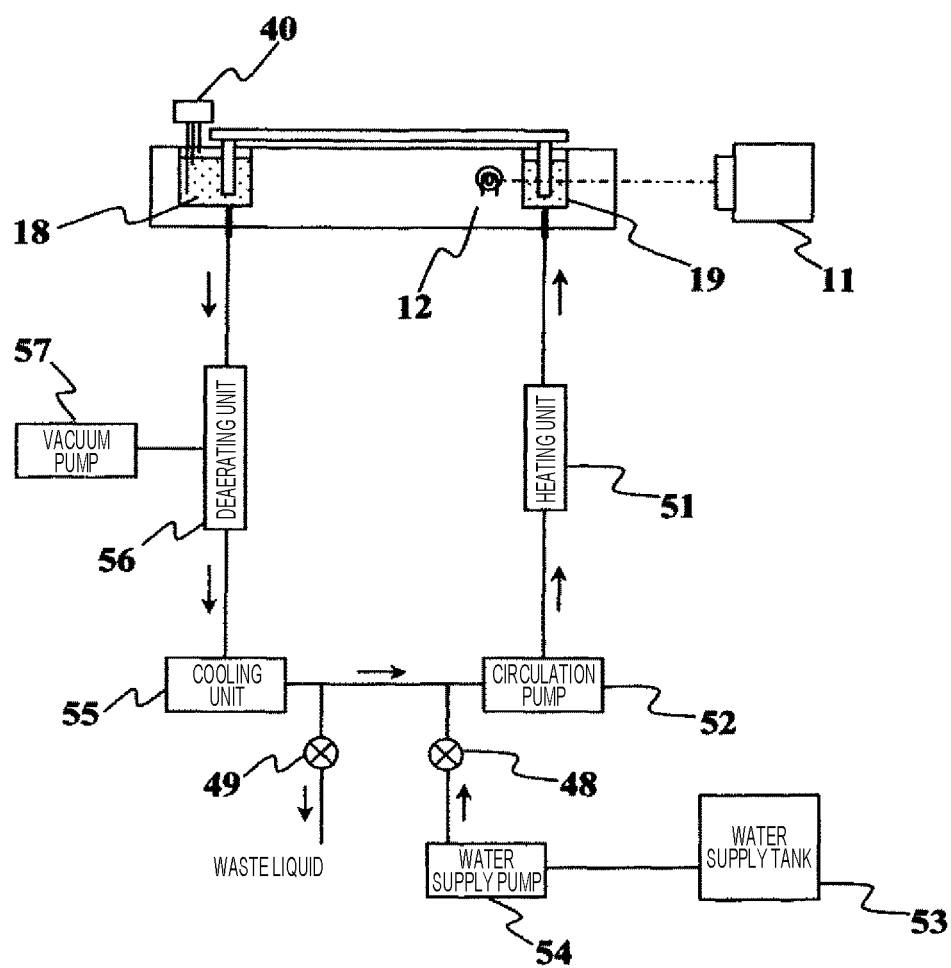
FIG. 3 is a diagram of an exemplary circulation flow passage of the reaction vessel water in the automatic analysis apparatus according to one embodiment of the present invention.

FIG. 3 is a diagram of an exemplary circulation flow passage of the reaction vessel water 18 in the reaction vessel 19. In FIG. 3, the water is supplied from a water supply tank 53 to the reaction vessel circulation flow passage by opening a water supply electromagnetic valve 48 and operating a water supply pump 54. Also, the water is drained from the circulation flow passage by opening a drain electromagnetic valve 49.

By operating a circulation pump 52, the water in the reaction vessel circulation flow passage reaches the circular reaction vessel 19 via a heating unit 51 and is circulated in the circulation flow passage via a deaerating unit 56 and a cooling unit 55. The deaerating unit 56 is connected to a vacuum pump 57.

In the automatic analysis apparatus, when the reaction vessel water replacement is instructed, the drain electromagnetic valve 49 is opened for a certain time to replace the reaction vessel water 18 in the reaction vessel 19. Accordingly, the reaction vessel water 18 in the reaction vessel 19 is drained outside from a drain port through a drain pipe.

After that, the reaction vessel water 18 is supplied from a water supply port to the reaction vessel 19 through a water supply pipe by closing the drain electromagnetic valve 49, operating the water supply pump 54, and opening the water supply electromagnetic valve 48. When it is confirmed by the first water level detector 41 that the reaction vessel water 18 in the reaction vessel 19 has reached a full water level 44 in the reaction vessel 19, the water supply is stopped by closing the water supply electromagnetic valve 48 and stopping the water supply pump 54.

In this way, the reaction vessel water 18 in the reaction vessel 19 can be replaced at one time. After the water replacement, in order to defoam and improve an antibacterial activity and electrical conductivity, a predetermined amount of surfactant is dispensed from the reagent container 26 placed in the reagent moving mechanism 31 to the reaction vessel 19 by the reagent dispenser 25 so that the surfactant concentration in the reaction vessel 19 becomes a predetermined concentration.

According to conditions such as shapes of the reaction vessel 19 and the circulated water flow passage of the reaction vessel 19 and a draining method, a part of water remains in the flow passage. Therefore, an actual water replacement rate is about 70% to 95%.

On the other hand, in an operation state in which the photometer continuously measures the specimen, the photometer 11 measures the absorbance of reaction liquid 17 dispensed in the reaction container 20 when the reaction container 20 crosses the optical axis 47 of the light emitted from the light source lamp 12. Therefore, when the water level of the reaction vessel water 18 is lowered below the optical axis 47, the optical axis 47 does not pass through the reaction vessel water 18. Therefore, the obtained absorbance is not a desired value.

Therefore, a measurement limit water level 45 of the photometer 11 is provided at a position lower than the full water level and higher than the optical axis 47, and the second water level detector 42 detects it.

That is, in the operation state, by opening the drain electromagnetic valve 49 to replace the reaction vessel water 18 in the reaction vessel 19, all the reaction vessel water 18 in the reaction vessel 19 is drained outside from the drain port through the drain pipe. After that, when it is confirmed by the second water level detector 42 that the water level has reached the measurement limit water level 45, the drain electromagnetic valve 49 is closed.

Next, the reaction vessel water 18 is supplied from the water supply port into the reaction vessel 19 through the water supply pipe by operating the water supply pump 54 and opening the water supply electromagnetic valve 48. When it can be confirmed by the first water level detector 41 that the reaction vessel water 18 in the reaction vessel 19 reaches the full water level 44, the water supply is stopped by closing the water supply electromagnetic valve 48 and stopping the water supply pump 54.

In this way, a part of the reaction vessel water 18 in the reaction vessel 19 can be replaced. The water may be drained while being supplied. Also, the water may be supplied while being drained. According to this operation, an amount of water which is partially replaced at one time can be adjusted.

A ratio r of the reaction vessel water 18 which can be replaced at one time to the whole amount of water can be represented by the following formula (1).

$$r = (Ha - Hb) \div Ha \tag{1}$$

Here, Ha represents the height of the full water level, and Hb represents the height of the measurement limit water level.

Also, when it is assumed that the number of times to partially replace the reaction vessel water 18 be n, a water replacement rate R of the reaction vessel 19 which has been replaced n times and a water consumption W in a case where the full water amount of the reaction vessel 19 is one can be obtained from the following formulas (2) and (3).

$$R = 1 - (1 - r)^n \tag{2}$$

$$W = n \times r \tag{3}$$

When it is assumed that the ratio r of the reaction vessel water 18 which can be replaced at one time relative to the whole amount of water be 0.2 (20%) and n be 12, the water replacement rate R and the water consumption W are represented by the following formulas (4) and (5).

$$R = 1 - (1 - 0.2)^{12} \tag{4}$$

$$W = 12 \times 0.2 = 2.4 \tag{5}$$

That is, the water replacement rate R becomes substantially 0.93 (93%) by partially replacing the reaction vessel water 18 twelve times per day, and the water of substantially 93% in the reaction vessel 19 can be replaced.

However, the water consumption is increased in proportion to the increase in the number of times to partially replace the reaction vessel water 18. To reduce the water consumption W, it is preferable that the water replacement rate r per time be improved and the number of times of water replacement n be reduced.

In a state other than the operation state, the photometer 11 does not continuously perform the measurement. In the above state, the optical axis 47 does not necessarily pass through the reaction vessel water 18. However, to maintain the temperature of the measurement system including the reaction vessel water 18 to be constant in the reaction vessel 19, it is necessary to circulate the reaction vessel water 18. For the circulation of the reaction vessel water 18, a predetermined amount of water is required. Therefore, a circulation limit water level 46 of the reaction vessel water 18 is provided at a position lower than the optical axis 47 and higher than the bottom surface of the reaction vessel 19, and the third water level detector 43 detects it.

That is, in the state other than the operation state, by opening the drain electromagnetic valve 49 to replace the reaction vessel water 18 in the reaction vessel 19, the reaction vessel water 18 in the reaction vessel 19 is drained outside from the drain port through the drain pipe. After that, when it is confirmed by the third water level detector 43 that the reaction vessel water 18 has reached the circulation limit water level 46, the drain electromagnetic valve 49 is closed.

Next, the reaction vessel water 18 is supplied from the water supply port into the reaction vessel 19 through the water supply pipe by operating the water supply pump 54 and opening the water supply electromagnetic valve 48. When it can be confirmed by the first water level detector 41 that the reaction vessel water 18 in the reaction vessel 19 reaches the full water level 44, the water supply is stopped by closing the water supply electromagnetic valve 48 and stopping the water supply pump 54. In this way, a part of the reaction vessel water 18 in the reaction vessel 19 can be replaced.

A ratio s of the reaction vessel water 18, which can be replaced at one time in the state other than the operation state by using the third water level detector 43, relative to the whole amount of water is larger than the ratio r of the reaction vessel water 18, which can be replaced at one time in the operation state by using the second water level detector 42, relative to the whole amount of water.

When it is assumed that the ratio s of the reaction vessel water 18 which can be replaced at one time relative to the whole amount of water be 0.5 (50%) and n be four, the water replacement rate R and the water consumption W are represented by the following formulas (6) and (7).

$$R = 1 - (1 - 0.5)^4 \tag{6}$$

$$W = 4 \times 0.5 = 2.0 \tag{7}$$

That is, by partially replacing the reaction vessel water 18 four times per day, the water replacement rate R in the formula (6) is substantially 0.93 (93%). The water of substantially 93% in the reaction vessel 19 can be replaced, and the water consumption is reduced.

In this way, by switching close timings of the drain electromagnetic valve 49 in the operation state and the state other than the operation state, the water consumption can be reduced. Also, even in the operation state, the water in the circulation flow passage of the reaction vessel 19 can be intermittently and partially replaced at a plurality of number of times without interfering the measurement by the photometer 11.

Also, when the state is changed from the state other than the operation state to the operation state, for example, as a normal preparing movement for the operation, the reaction container moving mechanism 13 is returned to a predetermined position, the reaction container 20 and the dispensers 24 and 25 are cleaned, and blank light measurement of the reaction container 20 is performed. Therefore, a predetermined period of time is required for the actual analysis by the photometer 11.

A capacity to supply water to the reaction vessel 19 is provided so as to recover the water level from the circulation limit water level 46 to the measurement limit water level 45 of the photometer 11 within the predetermined period of time. Accordingly, even in the middle of the water replacement in the state other than the operation state and even when the water level of the reaction vessel has reached the circulation limit water level 46, the water level can be recovered during the operation preparing movement. Also, the measurement by the photometer can be performed without waiting for the water level recovery in the operation state.

When the water level of the reaction vessel water has not reached the measurement limit water level 45 of the photometer 11 in the operation state due to a lack of the capacity to supply water, it is possible to output an alarm to the CRT (display unit) 6 and wait for the measurement by the photometer 11 until the water level reaches the measurement limit water level 45.

Also, in the middle of the water replacement or after the water replacement, a surfactant is suctioned by the reagent dispenser 25 from the reagent container 26 placed in the reagent moving mechanism 31, and a predetermined amount of the suctioned surfactant is dispensed to the reaction vessel 19. Then, the surfactant concentration of the reaction vessel 19 becomes a predetermined concentration.

In this way, by intermittently replacing a part of the water in the reaction vessel 19 in the operation state and the state other than the operation state, all the water in the flow passage can be replaced within 24 hours without interfering the measurement by the photometer 11.

However, it is considered that the quality of the water in the reaction vessel 19 is changed by intermittently replacing the water in the flow passage and that the change affects the measurement. A traditional automatic analysis apparatus compares the absorbance of the cell blank water in each reaction container with the reference value and issues an alarm when the difference exceeds a predetermined value. However, since a part of the water is often replaced in the embodiment of the present embodiment, it is desired to compare values including changes with lapse of time regarding the same object.

Regarding a predetermined single reaction container 20, the measurement is not performed to the specimen, and the measurement is performed to the cell blank water. The absorbance of the cell blank water in the specific single reaction container 20 is measured, and the results are accumulated and stored in the memory 2. There are various methods to determine abnormal data. For example, there is a method for statistically determining obtained and measured values and issuing a warning when a distance from an average value exceeds a predetermined threshold.

Also, the object to be measured may be different from the cell blank water. The absorbance of liquid which is known may be measured by dispensing the specimen and reagent. In short, the absorbance of the water including the reaction vessel water 18 is measured before and after the replacement of the reaction vessel water, and the computer 1 determines the abnormality in the reaction vessel water replacement based on the measured value.

As a result, in a case where the abnormality in the reaction vessel water replacement has been detected, the computer (control unit) 1 determines that the absorbance measured during the reaction vessel water replacement is not accurately measured. Regarding the results obtained by measuring the specimen after when the abnormal reaction vessel water replacement has been started, a warning showing an abnormality of the water in the reaction vessel 19 is displayed on the CRT (display unit) 6.

Figure 4:
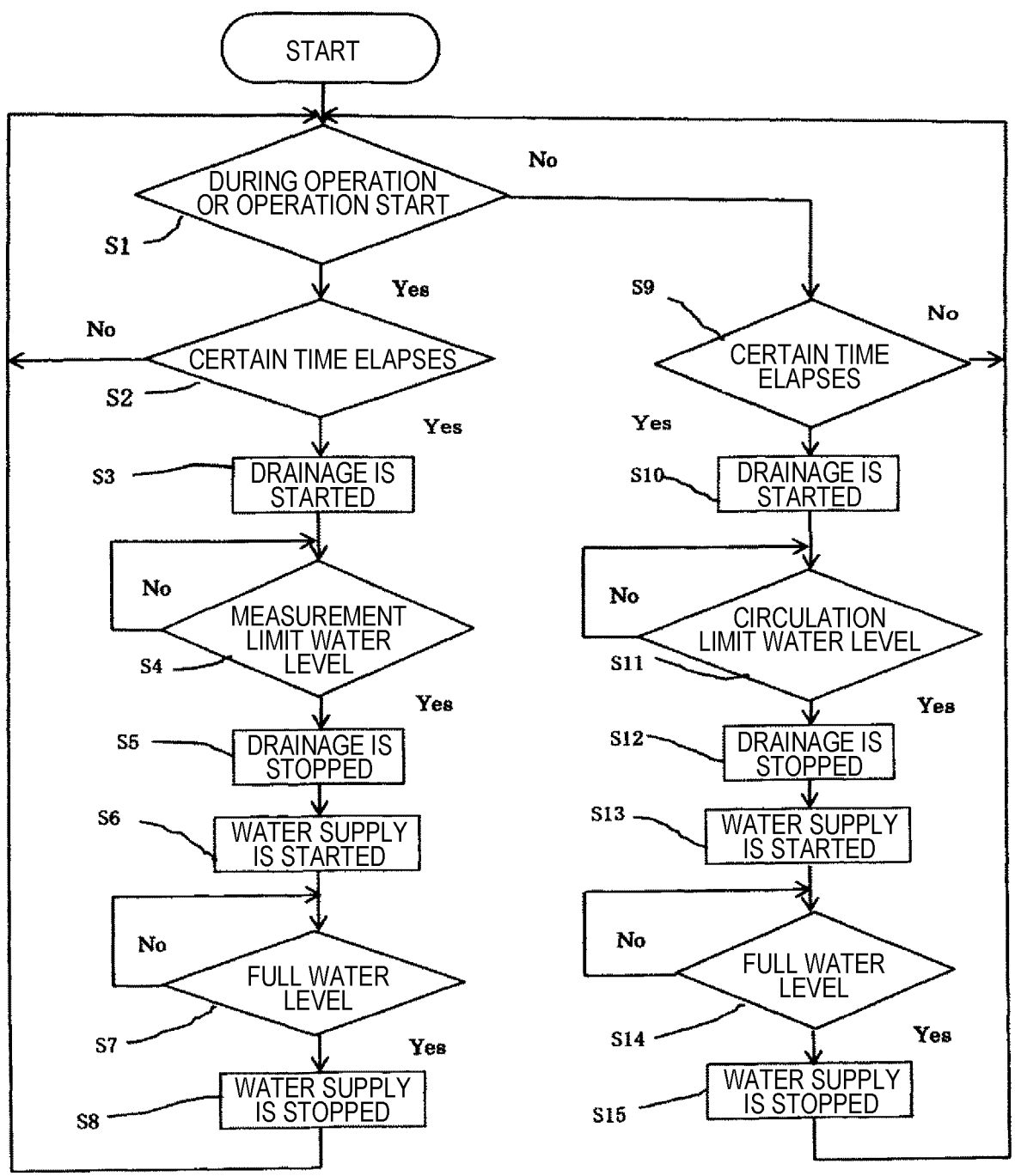
FIG. 4 is a flowchart of an operation to replace the reaction vessel water according to one embodiment of the present invention.

FIG. 4 is a flowchart of an operation to replace the reaction vessel water 19 according to one embodiment of the present invention. Also, FIG. 5 is a block diagram of an operation function of the computer 1 to replace the reaction vessel water 19 according to one embodiment of the present invention.

Figure 5:
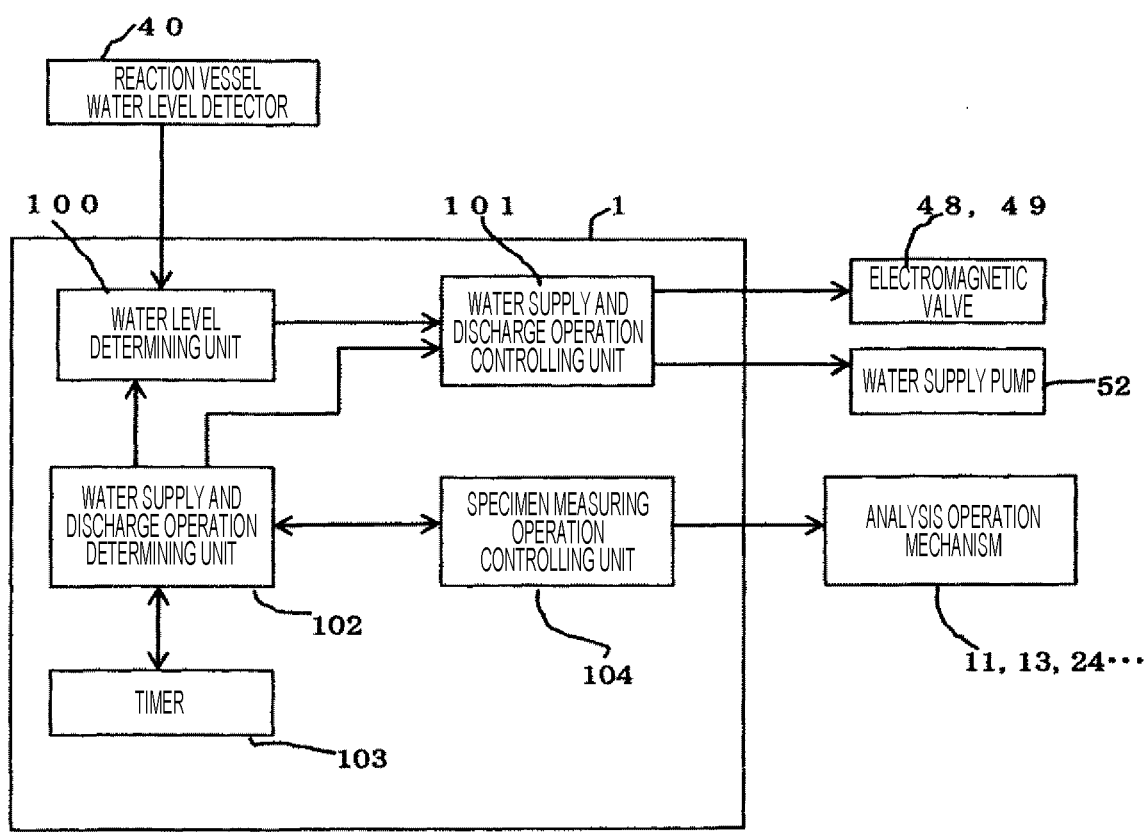
FIG. 5 is a block diagram of an operation function to replace the reaction vessel water according to one embodiment of the present invention.

In FIG. 5, a water level determining unit 100 determines the water level in the reaction vessel 19 based on a detection signal from the reaction vessel water level detector 40. A specimen measuring operation controlling unit 104 controls operations of the photometer 11, the reaction container moving mechanism 13, the specimen dispenser 24, and the reagent dispenser 25 which are analysis operation mechanisms.

A water supply and discharge operation determining unit 102 determines the state based on an operation control performed by the specimen measuring operation controlling unit 104. The states are: a state during the specimen measuring operation; a state where specimen measuring operation is started; or a state other than the above. A water supply and discharge operation controlling unit 101 controls operations of the electromagnetic valves 48 and 49 and the water supply pump 52 based on information from the water level determining unit 100 and the water supply and discharge operation determining unit 102.

In step S1 in FIG. 4, it is determined by the water supply and discharge operation determining unit 102 whether the automatic analysis apparatus is performing the operation or starts the operation. When it is determined in step S1 that the automatic analysis apparatus is performing the operation or starts the operation, a water supply and discharge operation during the measuring period is controlled.

The water supply and discharge operation determining unit 102 determines whether a certain period of time has elapsed at the present time with reference to a timer 103, that is, whether the water supply and discharge operation is to be started at the present time (step S2). When a certain period of time has not elapsed in step S2, the procedure returns to step S1.

When a certain period of time has elapsed in step S2, water drainage is started in step S3. According to an instruction from the water supply and discharge operation determining unit 102 to the water supply and discharge operation control unit 101, the water supply and discharge operation controlling unit 101 opens the electromagnetic valve 49 and starts to drain water.

Next, the water level determining unit 100 determines in step S4 whether the water level of the reaction vessel water 18 has reached the measurement limit water level 45. When the water level determining unit 100 has determined in step S4 that the water level of the reaction vessel water 18 has reached the measurement limit water level 45, the procedure proceeds to step S5. The water supply and discharge operation controlling unit 101 closes the electromagnetic valve 49 and stops draining the water. Subsequently, in step S6, the water supply and discharge operation controlling unit 101 starts to supply water by opening the electromagnetic valve 48 and operating the water supply pump 52.

Next, the water level determining unit 100 determines in step S7 whether the water level of the reaction vessel water 18 has reached the full water level 44. When the water level determining unit 100 has determined in step S7 that the water level of the reaction vessel water 18 has reached the full water level 44, the procedure proceeds to step S8. The water supply and discharge operation controlling unit 101 closes the electromagnetic valve 48 and stops the water supply pump 52. The procedure returns to step S1.

In step S1, when the automatic analysis apparatus is performing the operation, the procedure proceeds to step S2. The water supply and discharge operation determining unit 102 determines whether a certain period of time has elapsed at the present time with reference to the timer 103. According to this, as long as a certain period of time has not elapsed after the water supply and discharge operation has ended, the water supply and discharge operation is not started again.

When it is determined in step S1 that the automatic analysis apparatus is not performing the operation or does not start the operation, water supply and discharge operation control in a period other than the measuring period is performed.

The water supply and discharge operation determining unit 102 determines whether a certain time has elapsed at the present time with reference to the timer 103, that is, whether the water supply and discharge operation is to be started at the present time in a case where the state is not the operation state (step S9). When a certain period of time has not elapsed in step S9, the procedure returns to step S1.

When a certain period of time has elapsed in step S9, the water drainage is started in step S10. According to an instruction from the water supply and discharge operation determining unit 102 to the water supply and discharge operation control unit 101, the water supply and discharge operation controlling unit 101 opens the electromagnetic valve 49 and starts to drain water.

Next, the water level determining unit 100 determines in step S11 whether the water level of the reaction vessel water 18 has reached a circulated water limit water level 46. When the water level determining unit 100 has determined in step S11 that the water level of the reaction vessel water 18 has reached the circulated water limit water level 46, the procedure proceeds to step S12. The water supply and discharge operation controlling unit 101 closes the electromagnetic valve 49 and stops the water drainage operation. Subsequently, in step S13, the water supply and discharge operation controlling unit 101 starts to supply water by opening the electromagnetic valve 48 and operating the water supply pump 52.

Next, the water level determining unit 100 determines in step S14 whether the water level of the reaction vessel water 18 has reached the full water level 44. When the water level determining unit 100 has determined in step S14 that the water level of the reaction vessel water 18 has reached the full water level 44, the procedure proceeds to step S15. The water supply and discharge operation controlling unit 101 closes the electromagnetic valve 48 and stops the water supply pump 52. The procedure returns to step S1.

When the automatic analysis apparatus is not in the operation state in step S1, the procedure proceeds to step S9. The water supply and discharge operation determining unit 102 determines whether a certain period of time has elapsed at the present time with reference to the timer 103. According to this, as long as a certain period of time has not elapsed after the water supply and discharge operation has ended, the water supply and discharge operation is not started again.

As described above, according to the embodiment of the present invention, the full water level 44, the measurement limit water level 45 which is lower than the full water level 44 and higher than the optical axis 47 of the photometer 11, and the circulation limit water level 46 which is lower than the optical axis 47 and higher than the bottom surface of the reaction vessel 19 and which is the limit of the water level to circulate the reaction vessel water 18 in the reaction vessel 19 are set as the water level in the reaction vessel 19. The reaction vessel water level detector 40 is provided which detects that the reaction vessel water 18 in the reaction vessel 19 has reached the full water level 44, the measurement limit water level 45, and the circulation limit water level 46. During the specimen measuring operation, the reaction vessel water 18 is reduced by draining the water from the full water level 44 to the measurement limit water level 45. After that, the reaction vessel water 18 is supplied to the full water level 44, and the reaction vessel water 18 is replaced.

Therefore, the reaction vessel water 18 can be replaced without interrupting the specimen measurement.

Also, in the state where the specimen measuring operation is not performed, the reaction vessel water 18 is reduced by draining it from the full water level 44 and the circulation limit water level 46. After that, the reaction vessel water 18 is supplied to the full water level 44. The reaction vessel water 18 is replaced in this way.

Therefore, in a state where the circulation of the reaction vessel water 18 in the reaction vessel 19 is maintained, a replacement rate of the reaction vessel water 18 per time is improved, and the consumption of the reaction vessel water 18 can be reduced.

The example illustrated in FIG. 4 indicates a case where the water supply is started after the water discharge ends. However, when the water supply and discharge are concurrently started, it is preferable that step S6 in FIG. 4 be moved between steps S3 and S4 and step S13 be moved between steps S10 and S11.

Also, in the above example, the third water level detector 43 for detecting the circulation limit water level 46 is provided, and the reaction vessel water 18 is replaced at the time other than the operation state. In another example, the third water level detector 43 is omitted, and the reaction vessel water 18 is replaced during the operation or at the start of the operation, and the water is not replaced at the time other than the operation state. This example also belongs the technical scope of the present invention.

In addition, in still another example, regardless of whether the state is the operation state or not, the water is drained from the full water level 44 to the measurement limit water level 45 and is controlled to be supplied from the measurement limit water level 45 to the full water level 44 at a predetermined frequency. This example also belongs the technical scope of the present invention.

REFERENCE SIGNS LIST

1 . . . computer,
2 . . . memory,
3 . . . hard disk,
5 . . . keyboard,
6 . . . CRT (display unit),
7 . . . interface,
11 . . . photometer,
12 . . . light source lamp,
13 . . . reaction container moving mechanism,
17 . . . reaction liquid, 18 . . . reaction vessel water (circulated water),
19 . . . reaction vessel,
20 . . . reaction container,
21 . . . specimen container,
22 . . . specimen moving mechanism,
23 . . . specimen information reader/writer,
24 . . . specimen dispenser,
25 . . . reagent dispenser,
26 . . . reagent container,
28 . . . reagent information reader/writer,
29, 33 . . . A/D converter,
30 . . . specimen container height detector,
31 . . . reagent moving mechanism,
32, 34 . . . driving unit,
40 . . . reaction vessel water level detector,
41 . . . first water level detector,
42 . . . second water level detector,
43 . . . third water level detector,
44 . . . full water level,
45 . . . measurement limit water level,
46 . . . circulation limit water level,
47 . . . optical axis,
48 . . . water supply electromagnetic valve,
49 . . . drain electromagnetic valve,
51 . . . heating unit,
52 . . . circulation pump,
53 . . . water supply tank,
54 . . . water supply pump,
55 . . . cooling unit,
56 . . . deaerating unit,
57 . . . vacuum pump,
100 . . . water level determining unit,
101 . . . water supply and discharge operation controlling unit,
102 . . . water supply and discharge operation determining unit,
103 . . . timer,
104 . . . specimen measuring operation controlling unit

The invention claimed is:

1. An automatic analysis apparatus comprising:
a reaction container moving mechanism including a reaction vessel configured to hold water and a plurality of reaction containers for containing a specimen and a reagent arranged in the reaction container moving mechanism and which are immersed in the water in the reaction vessel, and the reaction container moving mechanism is configured to move the reaction containers thereon;
a light source lamp configured to irradiate a reaction container among the plurality of reaction containers arranged in the reaction vessel of the reaction container moving mechanism with light;
a photometer configured to measure the light emitted from the light source lamp and passed through the reaction container;
a discharge mechanism configured to discharge the water in the reaction vessel;
a water supply mechanism configured to supply water into the reaction vessel;
a reaction vessel water level detector including a first water level detector configured to detect that a water level of the water in the reaction vessel is a full water level and a second water level detector configured to detect that the water level of the water in the reaction vessel is a measurement limit water level which is lower than the full water level and higher than a position of an optical axis of the light emitted from the light source lamp; and
a control unit connected to the reaction container moving mechanism, the light source lamp, the photometer, the discharge mechanism, and the water supply mechanism, the control unit programmed to control operations of the reaction container moving mechanism, the light source lamp, and the photometer to analyze the specimen in the reaction container, and programmed to control operations of the discharge mechanism and the water supply mechanism based on the water level of the reaction vessel water detected by the reaction vessel water level detector.

2. The automatic analysis apparatus according to claim 1, wherein
the control unit is programmed to perform a reaction vessel water replacing operation in which the water in the reaction vessel is drained to the measurement limit water level by controlling the discharging mechanism when the water level of the water in the reaction vessel is the full water level, and the water is supplied to the full water level by controlling the water supply mechanism when the water level of the water in the reaction vessel reaches the measurement limit water level.

3. The automatic analysis apparatus according to claim 2, wherein
the reaction vessel water level detector further includes a third water level detector configured to detect that the water level of the water in the reaction vessel is a circulation limit water level which is lower than the measurement limit water level and higher than a bottom surface of the reaction vessel,
the control unit is programmed to:
in a measuring period when the photometer measures the light passed though the reaction container, perform a water supply and discharge operation control in which the water in the reaction vessel is drained until the water level of the water in the reaction vessel reaches the measurement limit water level by controlling the discharging mechanism when the water level of the water in the reaction vessel is the full water level, and the water is supplied into the reaction vessel until the water level in the reaction vessel reaches the full water level by controlling the water supply mechanism when the water level of the water in the reaction vessel reaches the measurement limit water level, and
in a period other than the measuring period perform a water supply and discharge operation control in which the water is drained until the water level of the water in the reaction vessel reaches the circulation limit water level by controlling the discharging mechanism when the water level of the water in the reaction vessel is the full water level, and the water is supplied until the water level of the water in the reaction vessel reaches the full water level by controlling the water supply mechanism when the water level of the water in the reaction vessel reaches the circulation limit water level.

4. The automatic analysis apparatus according to claim 3, wherein
the control unit is programmed to repeat the water supply and discharge operation control during the measuring period at a predetermined frequency.

5. The automatic analysis apparatus according to claim 3, wherein the control unit is programmed to repeat the water supply and discharge operation control in the period other than the measuring period at a predetermined frequency.

6. The automatic analysis apparatus according to claim 3, wherein
the circulation limit water level is set to be a level at which the water supply mechanism is capable of supplying water to the reaction vessel from the circulation limit water level to the measurement limit water level in a period of time from the period when the photometer does not perform the measurement to a start of the measuring period by the photometer.

7. The automatic analysis apparatus according to claim 3, wherein
the control unit is programmed to, in a case where the water supply and discharge operation control in a period other than the measuring period is performed and the water level in the reaction vessel is lower than the measurement limit water level, control the photometer to wait until the water level in the reaction vessel reaches the measurement limit water level restart the measurement of the light.

8. The automatic analysis apparatus according to claim 2, further comprising:
a reagent dispenser configured to dispense a reagent to the reaction container,
wherein the control unit is programmed to, after performing the reaction vessel water replacing operation, control the reagent dispenser to suction a surfactant to defoam and improve an antibacterial activity and electrical conductivity and discharge the surfactant in the reaction vessel.

9. The automatic analysis apparatus according to claim 2, further comprising:
a display unit,
wherein another reaction container, for containing liquid of which an absorbance is known, is immersed in the water in the reaction vessel, and
wherein the control unit is programmed to:
control the photometer to measure the absorbance of the liquid in the other reaction container immersed in the water in the reaction vessel of the reaction container moving mechanism,
determine whether the reaction vessel water is abnormal by comparing the measured absorbance with the known absorbance, and
cause the display unit to display a warning when the reaction vessel water is determined to be abnormal.

* * * * *